US012779232B2

(12) United States Patent
Armesto et al.

(10) Patent No.: US 12,779,232 B2
(45) **Date of Patent: *Nov. 3, 2026**

(54) IMPLANTABLE MEDICAL DEVICE WITH MACHINED ENCLOSURE

(71) Applicant: Greatbatch Ltd., Clarence, NY (US)

(72) Inventors: Ignacio Agustin Armesto, Montevideo (UY); Luis Daniel Villamil, Montevideo (UY); Fernando Escotto, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 658 days.

This patent is subject to a terminal disclaimer.

(21) Appl. No.: 18/134,071

(22) Filed: Apr. 13, 2023

(65) Prior Publication Data

US 2023/0330424 A1 Oct. 19, 2023

Related U.S. Application Data

(60) Provisional application No. 63/331,268, filed on Apr. 15, 2022.

(51) Int. Cl.
*A61N 1/375* (2006.01)

(52) U.S. Cl.
CPC .................................. *A61N 1/3758* (2013.01)

(58) Field of Classification Search
CPC ... A61N 1/3758; A61N 1/375; A61N 1/37512
See application file for complete search history.

(56) References Cited

U.S. PATENT DOCUMENTS

| | | | | |
|---|---|---|---|---|
| 5,250,373 | A * | 10/1993 | Muffoletto | H01M 4/70 429/233 |
| 5,431,695 | A | 7/1995 | Wiklund et al. | |
| 5,535,097 | A | 7/1996 | Ruben et al. | |
| 5,877,472 | A | 3/1999 | Campbell et al. | |
| 6,006,133 | A | 12/1999 | Lessar et al. | |
| 6,799,072 | B2 | 9/2004 | Ries et al. | |
| 6,931,284 | B2 | 8/2005 | Engmark et al. | |
| 7,110,240 | B2 | 9/2006 | Breyen et al. | |
| 7,271,994 | B2 * | 9/2007 | Stemen | H01G 9/06 29/25.03 |
| 7,322,832 | B2 | 1/2008 | Kronich et al. | |
| 7,713,656 | B2 | 5/2010 | Zhao et al. | |
| 7,733,631 | B2 | 6/2010 | Brabeck et al. | |
| 7,761,165 | B1 | 7/2010 | Haller et al. | |
| 8,694,101 | B2 | 4/2014 | Austin | |
| 9,259,574 | B2 | 2/2016 | Aghassian et al. | |
| 9,381,368 | B2 | 7/2016 | Ranpura et al. | |
| 9,757,573 | B2 | 9/2017 | Glynn et al. | |
| 10,279,187 | B2 | 5/2019 | Vandenburg | |
| 11,040,210 | B2 | 6/2021 | Lim et al. | |

(Continued)

*Primary Examiner* — Eugene T Wu
(74) *Attorney, Agent, or Firm* — Hodgson Russ LLP

(57) ABSTRACT

In various examples, an enclosure for an implantable medical device includes a first enclosure portion and a second enclosure portion, wherein at least the first enclosure portion and the second enclosure portion are joined together to form the enclosure. At least one feature is configured for attachment of at least one component of the implantable medical device to the enclosure. The at least one feature is integrally formed with the enclosure. In some examples, the enclosure is formed by machining.

7 Claims, 4 Drawing Sheets

(56) References Cited

U.S. PATENT DOCUMENTS

| | | | | |
|---|---|---|---|---|
| 11,219,776 | B2 | 1/2022 | Henschel et al. | |
| 2004/0064163 | A1* | 4/2004 | Aamodt ................. | A61N 1/378 607/36 |
| 2019/0358459 | A1 | 11/2019 | Baade et al. | |
| 2021/0213284 | A1 | 7/2021 | Williams et al. | |
| 2022/0001186 | A1 | 1/2022 | Lim et al. | |

* cited by examiner

IMPLANTABLE MEDICAL DEVICE WITH MACHINED ENCLOSURE

CROSS REFERENCE TO RELATED APPLICATION

This application claims the benefit of priority to U.S. Provisional Application Ser. No. 63/331,268, filed on Apr. 15, 2022, entitled "IMPLANTABLE DEVICE MACHINED ENCLOSURE WITH INNER FEATURES," which is incorporated by reference herein in its entirety.

BACKGROUND

Implantable medical devices typically include stamped metallic enclosures. Such stamped enclosures do not allow for the inclusion of integral features (whether simple or complex) associated with them because the stamping process used to make them does not allow for the implementation of such integral features. The stamping process typically requires the enclosures to have relatively smooth, simple surfaces, especially with respect to walls of the enclosure that are generally parallel to a stamping direction of the stamping process.

Because conventional stamped enclosures do not allow for integral features (for instance, integral features associated with the enclosure to which to attach components of the implantable medical device), additional, separate, non-integral structures are often used to attach components of the implantable medical device to the enclosure. For instance, a plastic nest is often used inside of a stamped enclosure of a device to fix or maintain in place one or more inner electronic components of the device, as well as any other component of the device. A titanium strip is often used to protect one or more inner electrical components when welding closed a port of the enclosure from outside of the enclosure. A separate component is often used with an enclosure in order to attach a lead stack assembly to an exterior of the enclosure. Additionally, some enclosures are required to be attached to a patient (for instance, a skull of a patient) using fasteners. Such enclosures often require a separate nest or cradle that is attached to the enclosure that then can be attached to the patient (such as using fasteners to attach the nest to a skull of the patient).

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to provide an enclosure for a medical device including integral features of the enclosure configured to fix, maintain, and/or self-center inner components of the medical device and remove the need for (or at least to reduce the size or importance of) a plastic nest within the enclosure. In various examples, such integral features can reduce assembly processes and therefore improve yield with respect to the enclosure. In some examples, the present subject matter is advantageous in that it provides for the addition of inner features to metallic enclosures by manufacturing them through machining, in some examples, in order to reduce, if not eliminate, the need for one or more inner components of the medical device. In some examples, the present invention facilitates reduction of overall volume of the medical device, reduction of the number of assembly stages for the medical device, and/or mitigation of assembly risks that can compromise quality of the medical device. To better illustrate the devices and methods described herein, a non-limiting list of examples is provided here:

Example 1 can include subject matter that can include an enclosure for an implantable medical device. The implantable medical device includes at least one component. The enclosure includes a first enclosure portion and a second enclosure portion, wherein at least the first enclosure portion and the second enclosure portion are joined together to form the enclosure. At least one feature is configured for attachment of the at least one component of the implantable medical device to the enclosure. The at least one feature is integrally formed with the enclosure.

In Example 2, the subject matter of Example 1 is optionally configured such that the enclosure is machined to integrally form the at least one feature with the enclosure.

In Example 3, the subject matter of Example 1 or 2 is optionally configured such that the at least one feature includes a shelf machined within at least one of the first enclosure portion and the second enclosure portion. The shelf is configured to support the at least one component of the implantable medical device.

In Example 4, the subject matter of Example 3 is optionally configured such that the at least one component includes an internal component of the implantable medical device.

In Example 5, the subject matter of any one of Examples 1-4 is optionally configured such that the at least one feature includes at least one attachment tab machined within at least one of the first enclosure portion and the second enclosure portion. The at least one attachment tab is configured to attach the implantable medical device to a patient.

In Example 6, the subject matter of any one of Examples 1-5 is optionally configured such that the at least one feature includes at least one external attachment member formed on an exterior of at least one of the first enclosure portion and the second enclosure portion. The at least one external attachment member is configured to attach the at least one component to an exterior of the enclosure of the implantable medical device.

In Example 7, the subject matter of Example 6 is optionally configured such that the at least one external attachment member includes at least one lead stack assembly attachment member machined within the exterior of at least one of the first enclosure portion and the second enclosure portion. The at least one lead stack assembly attachment member is configured to attach the at least one component of the implantable medical device, wherein the at least one component includes a lead stack assembly.

In Example 8, the subject matter of Example 6 or 7 is optionally configured such that the at least one external attachment member includes at least header attachment member machined within the exterior of at least one of the first enclosure portion and the second enclosure portion. The at least header attachment member is configured to attach the at least one component of the implantable medical device, wherein the at least one component includes a header.

In Example 9, the subject matter of any one of Examples 1-8 is optionally configured such that the at least one feature includes a weld protection feature machined within at least one of the first enclosure portion and the second enclosure portion. The weld protection feature is configured to protect an interior of the implantable medical device during welding of a fill port of the enclosure.

In Example 10, the subject matter of Example 9 is optionally configured such that the weld protection feature includes a wall machined within the enclosure and positioned proximate the fill port of the enclosure. The wall is configured to inhibit weld debris from damaging an electronic component of the implantable medical device within the enclosure during welding of the fill port.

Example 11 can include, or can optionally be combined with any one of Examples 1-10 to include subject matter that can include an implantable medical device including an enclosure including a first enclosure portion and a second enclosure portion, wherein at least the first enclosure portion and the second enclosure portion are joined together to form the enclosure. At least one component is associated with the enclosure. At least one feature is configured for attachment of the at least one component to the enclosure. The at least one feature is integrally formed with the enclosure.

In Example 12, the subject matter of Example 11 is optionally configured such that the enclosure is machined to integrally form the at least one feature with the enclosure.

In Example 13, the subject matter of Example 11 or 12 is optionally configured such that the at least one feature includes a shelf machined within at least one of the first enclosure portion and the second enclosure portion. The at least one component includes an internal component of the implantable medical device. The shelf is configured to support the internal component of the implantable medical device within the enclosure.

In Example 14, the subject matter of any one of Examples 11-13 is optionally configured such that the at least one feature includes at least one attachment tab machined within at least one of the first enclosure portion and the second enclosure portion. The at least one attachment tab is configured to attach the implantable medical device to a patient.

In Example 15, the subject matter of any one of Examples 11-14 is optionally configured such that the at least one feature includes at least one external attachment member formed on an exterior of at least one of the first enclosure portion and the second enclosure portion. The at least external attachment member is configured to attach the at least one component to an exterior of the enclosure of the implantable medical device.

In Example 16, the subject matter of Example 15 is optionally configured such that the at least one external attachment member includes at least one of at least one lead stack assembly attachment member and at least one header attachment member. The at least one lead stack assembly attachment member is machined within the exterior of at least one of the first enclosure portion and the second enclosure portion. The at least one lead stack assembly attachment member is configured to attach the at least one component of the implantable medical device, wherein the at least one component includes a lead stack assembly. The at least one header attachment member is machined within the exterior of at least one of the first enclosure portion and the second enclosure portion. The at least header attachment member is configured to attach the at least one component of the implantable medical device, wherein the at least one component includes a header.

In Example 17, the subject matter of any one of Examples 11-16 is optionally configured such that the at least one feature includes a weld protection feature machined within at least one of the first enclosure portion and the second enclosure portion. The weld protection feature is configured to protect an interior of the implantable medical device during welding of a fill port of the enclosure, wherein the weld protection feature includes a wall machined within the enclosure and positioned proximate the fill port of the enclosure. The wall is configured to inhibit weld debris from damaging an electronic component of the implantable medical device within the enclosure during welding of the fill port, wherein a passageway is disposed between the wall and the enclosure.

Example 18 can include, or can optionally be combined with any one of Examples 1-17 to include subject matter that can include an implantable medical device including a machined enclosure including a first enclosure portion and a second enclosure portion, wherein at least the first enclosure portion and the second enclosure portion are joined together to form the enclosure. At least one component is associated with the enclosure. At least one feature is configured for attachment of the at least one component to the enclosure. The at least one feature is machined within at least one of the first and second enclosure portions to be integrally formed with the enclosure. The at least one feature including at least one of a shelf, at least one attachment tab, at least one external attachment member, and a weld protection feature. The shelf is machined within at least one of the first enclosure portion and the second enclosure portion. The at least one component includes an internal component of the implantable medical device. The shelf is configured to support the internal component of the implantable medical device within the enclosure. The at least one attachment tab is machined within at least one of the first enclosure portion and the second enclosure portion. The at least one attachment tab is configured to attach the implantable medical device to a patient. The at least one external attachment member is formed on an exterior of at least one of the first enclosure portion and the second enclosure portion. The at least one external attachment member is configured to attach the at least one component to an exterior of the enclosure of the implantable medical device. The weld protection feature is machined within at least one of the first enclosure portion and the second enclosure portion. The weld protection feature is configured to protect an interior of the implantable medical device during welding of a fill port of the enclosure.

In Example 19, the subject matter of Example 18 is optionally configured such that the at least one external attachment member includes at least one of at least one lead stack assembly attachment member and at least one header attachment member. The at least one lead stack assembly attachment member is machined within the exterior of at least one of the first enclosure portion and the second enclosure portion. The at least one lead stack assembly attachment member is configured to attach the at least one component of the implantable medical device, wherein the at least one component includes a lead stack assembly. The at least one header attachment member machined within the exterior of at least one of the first enclosure portion and the second enclosure portion, the at least header attachment member configured to attach the at least one component of the implantable medical device, wherein the at least one component includes a header.

In Example 20, the subject matter of Example 18 or 19 is optionally configured such that the weld protection feature includes a wall machined within the enclosure and positioned proximate the fill port of the enclosure. The wall being is to inhibit weld debris from damaging an electronic component of the implantable medical device within the enclosure during welding of the fill port, wherein a passageway is disposed between the wall and the enclosure.

DETAILED DESCRIPTION

Figure 1:
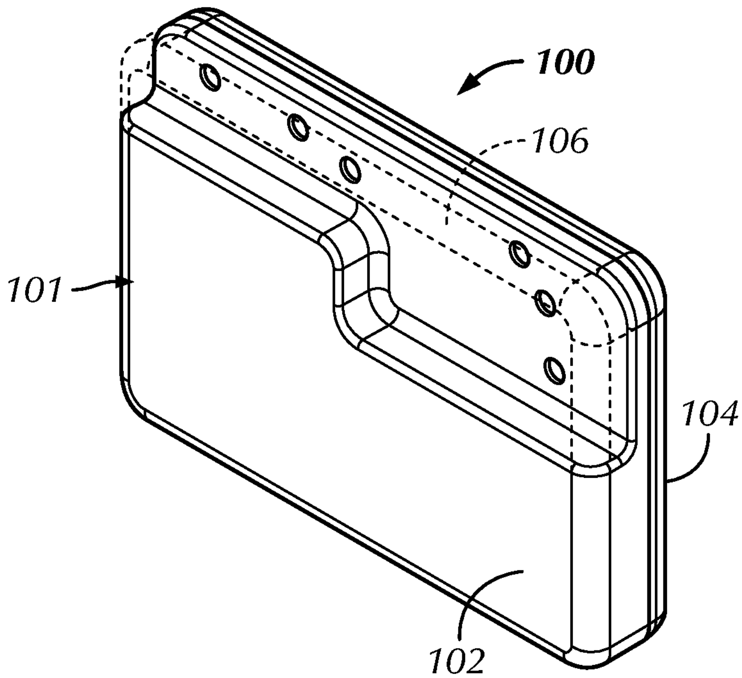
FIG. 1 is a perspective view of an enclosure for an implantable medical device, the enclosure being in accordance with at least one example of the invention.
Figure 2:
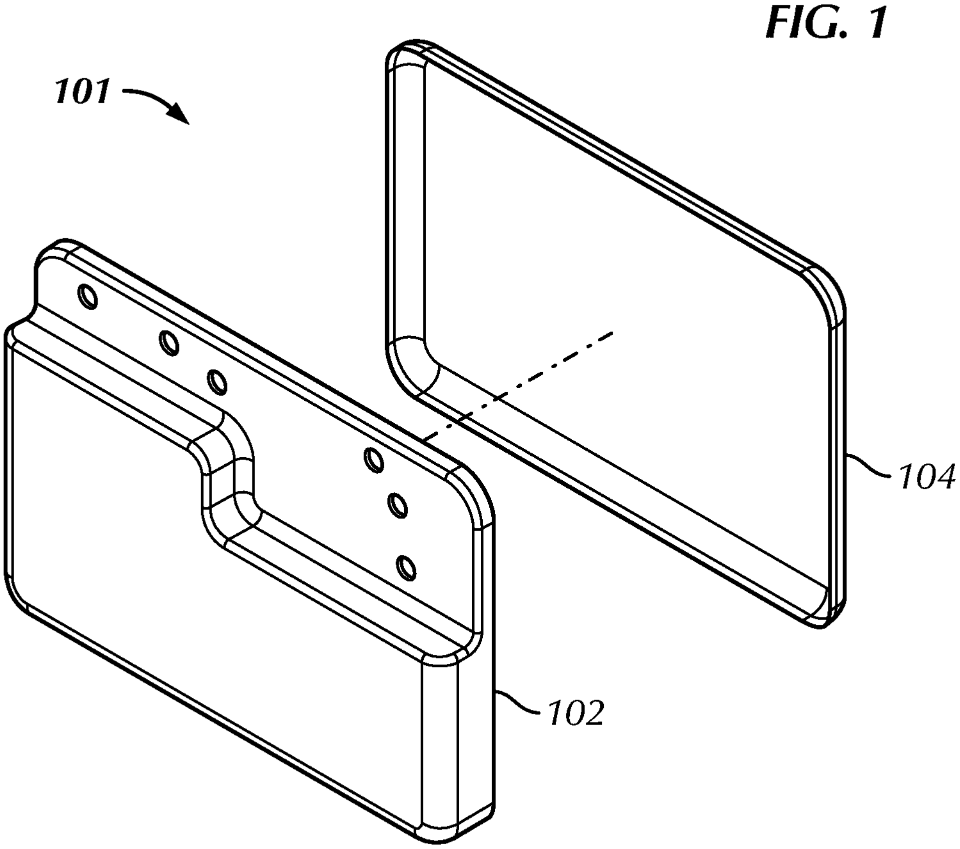
FIG. 2 is an exploded perspective view of the enclosure of FIG. 1.
Figure 3:
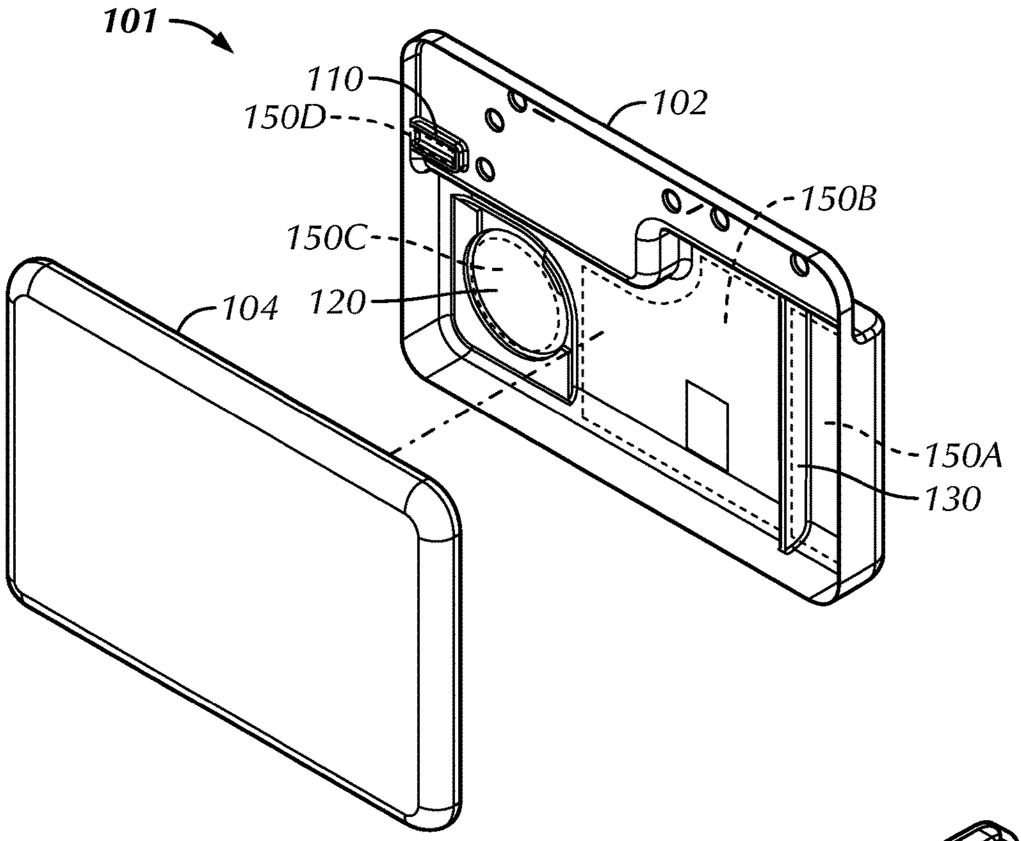
FIG. 3 is an exploded perspective view of the enclosure of FIG. 1.
Figure 4:
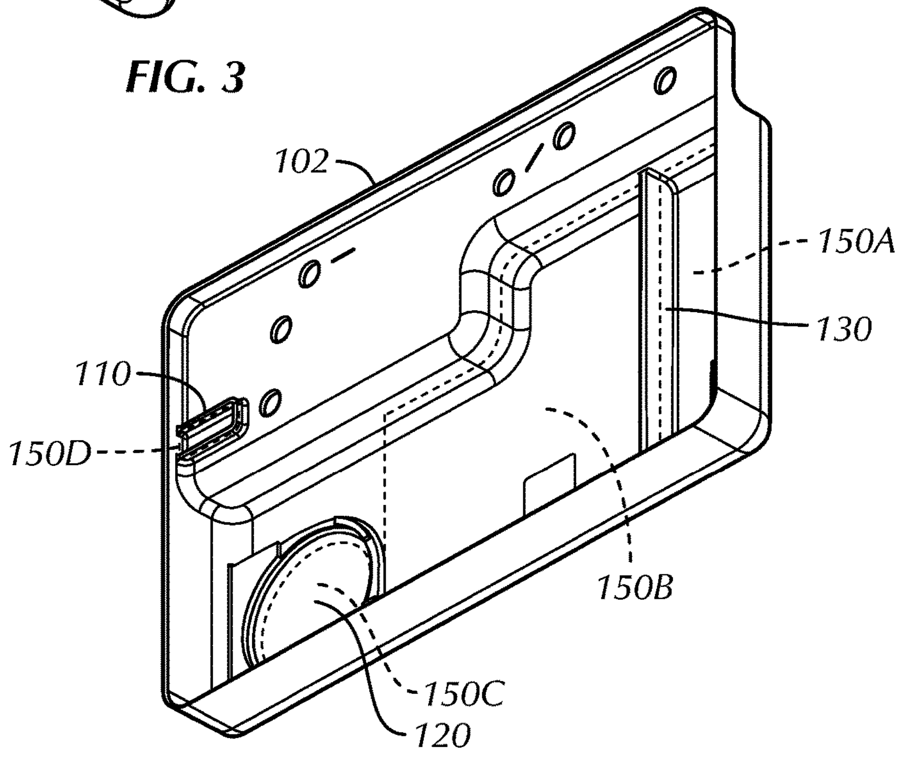
FIG. 4 is a perspective view of an enclosure portion of the enclosure of FIG. 1.

The present invention relates generally to an enclosure for a medical device. More specifically, the present invention relates to an enclosure for a medical device, the enclosure including one or more features integrally formed as part of the enclosure to fix, maintain, and/or self-center one or more components of the medical device within and/or to the enclosure, protect one or more inner components within the enclosure, and/or allow attachment of the medical device to a patient. In some examples, the present invention allows for a reduction of assembly processes and therefore improvement in yield with respect to the enclosure. In some examples, the present invention facilitates reduction of overall volume of the medical device, reduction of the number of assembly stages for the medical device, and/or mitigation of assembly risks that can compromise quality of the medical device.

In some examples, the present inventive subject matter allows for features that can add mechanical robustness (for example, ribs to lessen if not eliminate deformation caused by battery swelling) to a device and/or self-center a component (such as, but not limited to, a motor vibrator, a buzzer, and/or a piezoelectric component) during assembly of the device. In some examples, integral features for electrically connecting the enclosure to device electronics can be desirable for some therapies. Therefore, adding a connection to be soldered/welded into the electronics can be accomplished using a machined feature of the enclosure. In other examples, integral features of the enclosure can be used to mechanically fixate a lead in a device header. In some examples, an integral feature of a device enclosure can provide for protection of interior components from a welding process, such as protecting such components from weld debris and/or heat. Such a feature can eliminate the need for a separate weld band to be attached to the enclosure, as is commonly done with typical weld protection in conventional enclosures, or formed using sophisticated metal-forming processes, thereby reducing an assembly process for the device. In still other examples, integral features can be used to allow fixation of a device to a human body with the use of one or more fasteners (such as, but not limited to, bone screws). In further examples, such features can allow for a device to be fixed directly onto a bone of a patient. The present inventive subject matter, in various examples, is directed to an implantable device enclosure design that allows for a lower volume device, although it is not limited thereto, as it can be used for an enclosure of any size.

The purpose of the present inventive subject matter, in some examples, is to reduce the size of an implantable device (for instance, an implantable stimulation and/or sensing device) by removing the need for one or more of the inner parts or components typically used within medical device enclosures and/or outer parts used on an external portion of the medical device enclosures. In some examples, the present inventive subject matter can also be used to reduce the number of assembly operations for a medical device by reducing assembly risk and enhancing yield. The present inventive subject matter, in some examples, allows for a smaller device while, at the same time, allows for the fixation of inner and/or outer components of the device.

In some examples, the present inventive subject matter reduces the number of components needed within and/or on a medical device and, therefore, reduces the complexity of the assembly, reducing the assembly times. For instance, in some examples, the present inventive subject matter reduces, if not eliminates, the need of an inner fixating component (such as a plastic nest, for instance) to one or more inner components in place within an enclosure of the medical device. In some examples, the present inventive subject matter reduces, if not eliminates, the need for a weld protection band, which is typically used in conventional medical devices to protect one or more inner electrical components within the medical device during welding procedures performed on the device. The present inventive subject matter, in some examples, reduces, if not eliminates, the need to use a mechanical fixation connector on a device header in order to fixate a lead to the medical device with insertion of the lead within the medical device. In some examples, the present inventive subject matter allows for directly fixating the medical device to a bone or other structure of a patient using one or more fasteners (such as, for instance, screws), without the need for additional parts (and, therefore, more processes) associated with the medical device. In various examples, the present inventive subject matter allows for tighter tolerances on features that fix, maintain, and/or self-center one or more components with respect to the medical device, due to, at least in part, the fixing features being machined into or otherwise integrally formed with the enclosure instead of using plastic parts or other separate components, as is typically used in conventional medical devices. The present inventive subject matter, in some examples, modifies a device enclosure to add one or more fixation features/brackets integrally formed within or on the enclosure, which allow for positioning inner components of the device without the need of an extra part, such as, for instance, a plastic nest.

Conventional medical device systems typically use stamped metallic enclosures. Such stamped enclosures do not allow for the addition of internal and external integral features to their design because of their manufacturing process. The present inventive subject matter provides for a machined enclosure made out of, but not limited to, commercial pure titanium or titanium alloys, in some examples, which allows for the addition of one or more internal and/or external integral features to the enclosure. Specifically, in some examples, machining of the enclosure can be used to include one or more internal and/or external integral features within or to the enclosure. Such integral features are generally not possible to add to conventional stamped metallic enclosures. For instance, in some examples, the enclosure is cut from metal stock using traditional machining machines, such as, but not limited to, a computer numerical control (CNC) machine, to precision remove material from the metal stock in order to form the desired shape of the enclosure, and, while doing so, integrally form features such as, but not limited to, one or more of a shelf, a bracket, a weld protection feature, a lead attachment feature, or the like, or a combination thereof, within an interior or an exterior of the enclosure.

Since the present inventive subject matter allows for fixation of inner components using the enclosure fixing features, it reduces, if not eliminates, in some examples, the need for a plastic nest and extra assembly processes, thereby potentially reducing a volume of the device. The present inventive subject matter, in some examples, also eliminates the need for a separate weld protection band to protect the inner electrical components during different welding operations of the device. Instead, in some examples, an integral weld protection feature can be machined within the enclosure itself during manufacture of the enclosure. The present inventive subject matter, in some examples, eliminates the need for an external mechanical fixation connector on the device header, which is used to fixate the lead, by incorporating an integral fixation connector on the machined enclosure. The present inventive subject matter, in some examples, reduces, if not eliminates, the need for one or more welded brackets, pins, or the like disposed in the header area to enhance adhesion of a header to the enclosure, by machining or otherwise forming one or more brackets, pins, or the like directly into the enclosure of the implantable medical device. In case the device needs to be directly affixed to a patient (for instance, screwed directly onto the patient's bone), the present inventive subject matter, in some examples, allows for adding a female screw feature or other fixation feature on an exterior of the machined enclosure, thereby eliminating the need to add a new, separate part or component in order to secure the device.

Typically, enclosures of implantable medical devices are metallic and are made by a stamping process. There are two types of stamping used for conventional enclosures, which yield two types of conventional enclosures: deep drawn enclosures and shallow drawn enclosures. Both types of conventional enclosures require a simple and flat inner surface given their manufacturing process, which does not allow for integral internal features as part of the same stamping/forming operation.

For instance, a titanium strip is usually welded to the conventional device enclosure or lid to protect inner components from metallic ejections caused by the welding of a helium backfilling hole. In some instances, the weld band can be formed as part of the stamping process with an extra stamping step of the process. However, due to complexity that this extra stamping step of the stamping process adds in the design of the tooling and process, it is often preferred to weld a separate strip to the enclosure to act as a weld band. Typically, this weld band is welded to the enclosure as part of a preparation or is added in the device assembly.

A mechanical fixation connector can be used on a device header to fixate the lead to the device, once inserted. Such a mechanical fixation connector is typically a separate feature from the enclosure and is part of the lead cavity stack assembly inside the header. The fixation connector must be placed on the header with a specific position and orientation with respect to the enclosure and/or the header and have certain minimum distances with the enclosure itself for the electrical connectors.

For a typical medical device that is placed in a cavity formed in a skull, for instance, a metallic nest, separate from an enclosure of the medical device, is typically screwed onto or otherwise attached to the skull. Then, the enclosure of the medical device is typically placed on and clamped inside the nest to attach the medical device to the skull.

As described above, conventional stamped enclosures do not allow for the addition of integral features to inner walls of an implantable medical device. Therefore, a plastic nest is typically used to fix one or more inner components (for instance, a printed circuit board (PCB), a battery, a radio-opaque identifier (ROI), a buzzer, etc.) within a conventional stamped enclosure.

In some examples, a machined device enclosure allows for the addition of inner features within or on the enclosure to fix one or more inner components within an implantable medical device and lessen, if not eliminate, the need for a plastic nest (as well as any other preparation or fixation component) to the enclosure. In this way, no extra area is needed in order to accommodate different processes, therefore reducing a volume of the device. In some examples, a machined feature of an enclosure allows for tighter tolerances than those achieved in plastic parts or welding of other inner components into an enclosure, which can improve the quality of the general assembly by reducing risk and improving assembly yield. In some examples, by eliminating the plastic nest and/or any other bracket, a general assembly of the implantable medical device becomes simpler, which, in turn, can reduce device assembly time.

Referring to FIGS. 1-5C, in some examples, an implantable medical device 100 includes an enclosure 101 in accordance with the present inventive subject matter. The implantable medical device 100, in some examples, can include a header 106 attached to an exterior of the enclosure 101, which can include components such as, but not limited to, one or more of a bore hole for attachment to a lead, an electrode, an antenna, a communication component, or the like. In some examples, the implantable medical device 100 includes an implantable cardiac device, such as, for instance, a pacemaker, defibrillator, or the like. In other examples, the implantable medical device 100 includes an implantable neurostimulator. In still other examples, the implantable medical device 100 includes other implantable medical devices, such as, for instance, a deep brain stimulation device, a cochlear implant, a gastric stimulator, an insulin pump and/or blood glucose monitor, etc. It should be understood that the inventive concepts described herein can be applied to any implantable medical device and should not be limited to any particular type of implantable device.

In some examples, the enclosure 101 of the implantable medical device 100 includes one or more integral features for locating, fixing, or otherwise disposing of one or more components of the implantable medical device 100. In some examples, the one or more integral features include one or more features that are integrally formed with the enclosure 101. The enclosure 101, in some examples, is machined to integrally form the one or more features with the enclosure 101. In some examples, the one or more integral features include one or more internal integral features 110, 120, 130, 140, as are further described herein. In some examples, the at least one feature 110, 120, 130, 140 is integrally formed with the enclosure 101 and is configured for attachment of at least one component of the implantable medical device

100 to the enclosure 101. In some examples, one or more machined internal integral features 110, 120, 130 can be included within the enclosure 101 to locate, fix, or otherwise position one or more inner or internal components 150A, 150B, 150C, 150D of the implantable medical device 100 within the enclosure 101 and, therefore, lessen if not avoid the need of a fixating component, such as a plastic nest or any other welded/added fixation component. In other examples, the internal integral feature 140 can be included within the enclosure 101 to integrally attach weld protection within the enclosure 101 to protect components within the enclosure 101 during welding of the enclosure 101. Although the enclosure 101, in some examples, is contemplated as being machined, in other examples, the enclosure 101 can be formed in other ways, including, but not limited to, three-dimensional printing, metal injection molding, or the like, either instead of or in addition to machining.

In some examples, the enclosure 101 includes a first enclosure portion 102 and a second enclosure portion 104. In some examples, at least the first enclosure portion 102 and the second enclosure portion 104 are joined together to form the enclosure 101. In various examples, the first and second enclosure portions 102, 104 are joined together in various manners, including, but not limited to, one or more of welding, brazing, soldering, crimping, use of one or more adhesives, interference fit, or the like. In some examples, the enclosure 101 can include more than two portions joined together.

In some examples, the enclosure 101 includes the first and second enclosure portions 102, 104 sized and shaped to accommodate the one or more internal components 150A, 150B, 150C, 150D within the enclosure 101. The one or more internal components 150A, 150B, 150C, 150D can include various different components, depending upon the type of implantable medical device 100, including, but not limited to, one or more of a battery, a capacitor, a printed circuit board (PCB), a buzzer and/or other alarm, a radio-opaque identifier (ROI), a sensor, an antenna, or the like. Various examples of internal components 150A, 150B, 150C, 150D are discussed herein, but it should be understood that they are merely exemplary and that any type of component or combination of components can be used within the enclosure 101 depending upon the particular application of the implantable medical device 100.

In some examples, one or both of the first enclosure portion 102 and the second enclosure portion 104 includes the one or more internal integral features 110, 120, 130, 140. Although the example shown in FIGS. 1-5C portray the one or more internal integral features 110, 120, 130, 140 formed within the first enclosure portion 102, this is merely exemplary. In other examples, one or more of the internal integral features 110, 120, 130, 140 can be disposed within the second enclosure portion 104. In still other examples, one or more of the internal integral features 110, 120, 130, 140 can be disposed within both the first enclosure portion 102 and the second enclosure portion 104. In still other examples, one or some of the one or more internal integral features 110, 120, 130, 140 can be disposed within the first enclosure portion 102 and another or others of the one or more internal integral features 110, 120, 130, 140 can be disposed within the second enclosure portion 104.

In some examples, the internal integral feature 110 includes a radio-opaque identifier (ROI) support 110. In some examples, the ROI support 110 includes a channel, receptacle, shelf, or other protrusion sized and shaped to accept and support a radio-opaque identifier (ROI) 150D or other internal component within the enclosure 101 of the implantable medical device 100. In some examples, the enclosure 101 is machined to integrally form the ROI support 110 within the enclosure 101. In some examples, the ROI support 110 includes a shelf machined within at least one of the first enclosure portion 102 and the second enclosure portion 104, the shelf being configured to support the ROI 150D of the implantable medical device 100.

With the ROI support 110 disposed in a desired location with respect to the enclosure 101, in some examples, the ROI 150D can be fixed to or within the ROI support 110 in order to properly locate and place the ROI 150D within the enclosure 101. In some examples, the ROI 150D is fixed within the ROI support 110 using an adhesive, such as, for instance, epoxy. In other examples, the ROI support 110 can include one or more tabs to at least assist in retaining the ROI 150D within the ROI support 110. In still other examples, the ROI 150D can be fixed to the ROI support 110 using one or more fasteners. In this way, in some examples, the ROI support 110 can lessen, if not eliminate, the need for a plastic nest as a supporting mechanism within the implantable medical device 100 since the ROI support 110 allows for proper placement and fixation of the ROI 150D within the enclosure 101, thereby allowing for identification of the implantable medical device 100 using the ROI 150D.

In some examples, the internal integral feature 120 includes a buzzer support 120. In some examples, the buzzer support 120 includes a platform, receptacle, shelf, or other element sized and shaped to accept and support a buzzer 150C or other internal component within the enclosure 101 of the implantable medical device 100. In some examples, the enclosure 101 is machined to integrally form the buzzer support 120 within the enclosure 101. In some examples, the buzzer support 120 includes a shelf machined within at least one of the first enclosure portion 102 and the second enclosure portion 104, the shelf being configured to support the buzzer 150C of the implantable medical device 100.

With the buzzer support 120 disposed in a desired location with respect to the enclosure 101, in some examples, the buzzer 150C can be fixed to or within the buzzer support 120 in order to properly locate and place the buzzer 150C within the enclosure 101. In some examples, the buzzer support 120 is positioned within the enclosure 101 in a location to give optimal acoustics to the buzzer 150C to increase the likelihood that an alarm sounded by the buzzer 120 would be heard by a patient, physician, or other person nearby. In some examples, the buzzer 150C is fixed within the buzzer support 120 using an adhesive, such as, for instance, epoxy. In other examples, the buzzer support 120 can include one or more tabs to at least assist in retaining the buzzer 150C within the buzzer support 120. In still other examples, the buzzer 150C can be fixed to the buzzer support 120 using one or more fasteners. In this way, in some examples, the buzzer support 120 can lessen, if not eliminate, the need for a plastic nest as a supporting mechanism within the implantable medical device 100 since the buzzer support 120 allows for proper placement and fixation of the buzzer 150C within the enclosure 101.

In some examples, the internal integral feature 130 includes at least one shelf 130. In some examples, the shelf 130 includes a rib, elongate protrusion, wall, strengthened portion, or other element extending a distance within the enclosure 101. In some examples, the shelf 130 can be sized, positioned, and/or shaped to allow placement of at least a first internal component 150A within the enclosure 101 of the implantable medical device 100. In some examples, the first internal component 150A is supported within the enclosure 101 by the shelf 130. In some examples, the shelf 130 can be sized, positioned, and/or shaped to allow placement of at least a second internal component 150B in addition to or instead of the first internal component 150A within the enclosure 101 of the implantable medical device 100. The shelf 130, in some examples, supports the second internal component 150B. In other examples, the shelf 130 supports both of the first and second internal components 150A, 150B. In still other examples, the shelf 130 acts to maintain separation of the first and second internal components 150A, 150B. In some examples, the enclosure 101 can include more than one shelf 130. In some examples, the one or more shelves 130 of the enclosure can be used to support at least the first internal component 150A and/or the second internal component 150B. In various examples, the first and second internal components 150A, 150B can include various types of components, including, but not limited to, one or more of a printed circuit board (PCB), a battery, a capacitor, an antenna, a communications module, an electronic module, a sensor, a buzzer, or the like. In some examples, the enclosure 101 is machined to integrally form the shelf 130 within the enclosure 101. In some examples, the shelf 130 is machined within at least one of the first enclosure portion 102 and the second enclosure portion 104, the shelf 130 being configured to support at least one of the first and second internal components 150A, 150B of the implantable medical device 100.

In some examples, the shelf 130 can help compartmentalize an interior of the enclosure 101 to allow for proper placement of one or more of the first and second internal components 150A, 150B within the enclosure 101. The shelf 130, in some examples, can also promote insulation of the first interior component 150A from the second interior component 150B within the enclosure 101. The shelf 130, in some examples, can at least partially support one or more of the first and second internal components 150A, 150B within the enclosure 101. In some examples, one or more of the shelves 130 can be formed within one or both of the first enclosure portion 102 and the second enclosure portion 104. In this way, in some examples, the shelf 130 can lessen, if not eliminate, the need for a plastic nest as a supporting mechanism within the implantable medical device 100 since the shelf 130 allows for proper placement and fixation of one or more of the first and second internal components 150A, 150B within the enclosure 101. In further examples, the one or more shelves 130 can add mechanical robustness to the enclosure 101, which, in turn, can reduce deformation of the enclosure 101 in the event of battery swelling, for instance.

Figure 5A:
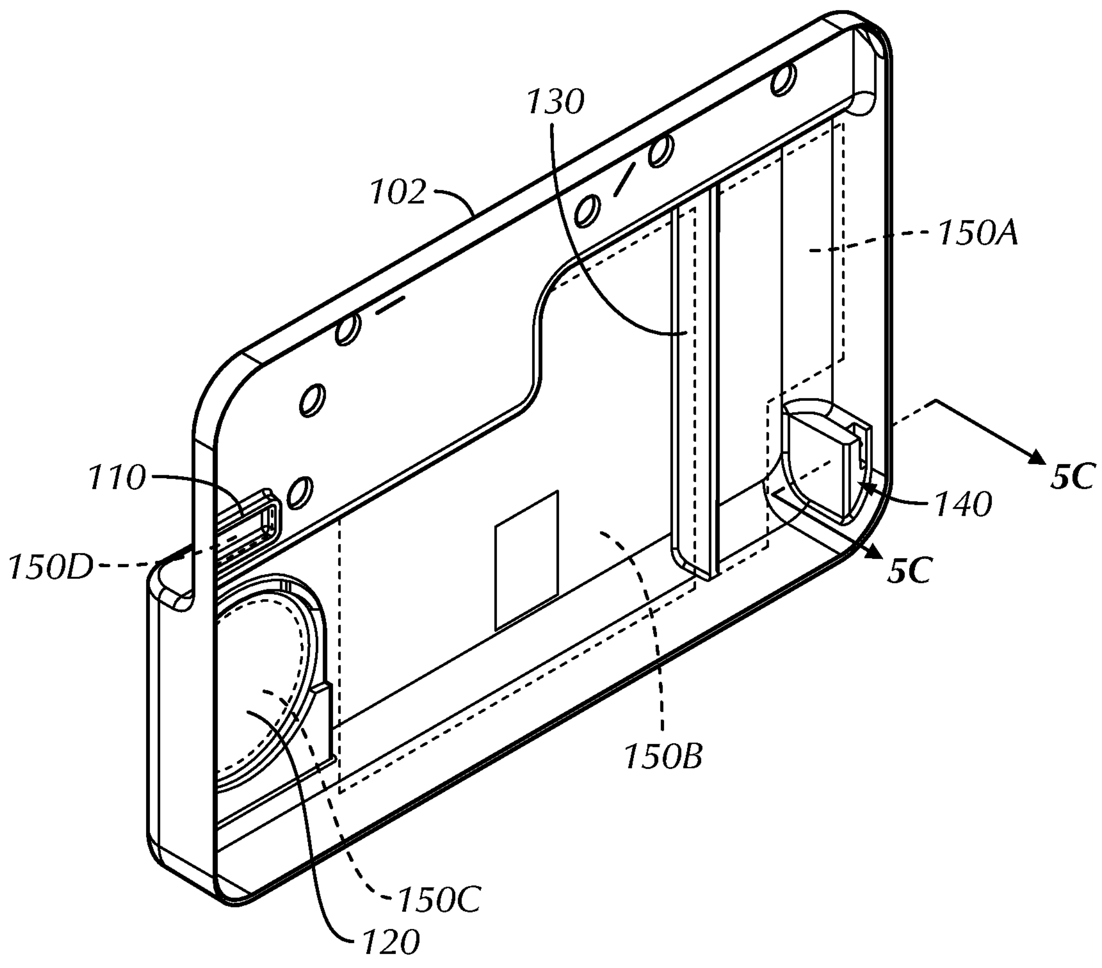
FIG. 5A is a perspective view of an enclosure portion for an implantable medical device, the enclosure portion being in accordance with at least one example of the invention.
Figure 5B:
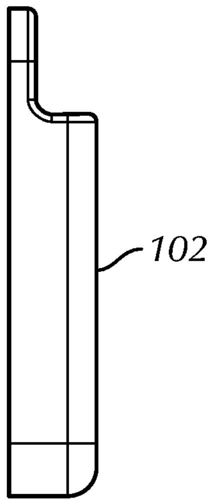
FIG. 5B is a side view of the enclosure portion of FIG. 5A.
Figure 5C:
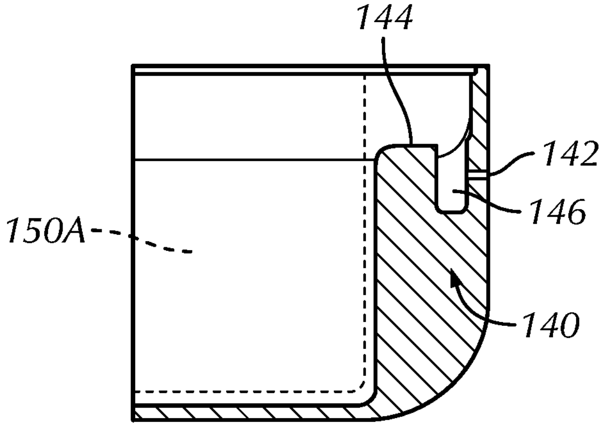
FIG. 5C is a cross-sectional view of the enclosure portion of FIG. 5A taken along line 5C-5C of FIG. 5A.

Referring specifically to FIGS. 5A-5C, in some examples, the internal integral feature 140 includes at least a weld protection feature 140. In some examples, the weld protection feature is integrally formed within at least one of the first enclosure portion 102 and the second enclosure portion 104. In further examples, the weld protection feature 140 is machined within at least one of the first enclosure portion 102 and the second enclosure portion 104. In some examples, the weld protection feature 140 is configured to protect an interior of the implantable medical device 100 during welding of a fill port 142 of the enclosure 101 of the implantable medical device 100. In some examples, the enclosure 101 of the implantable medical device 100 is backfilled with helium or another inert gas, for instance, to test the enclosure 101 for hermeticity. In such cases, the fill port 142 can be used to fill the enclosure 101 with helium or the like. After filling, the fill port 142 can be welded closed to seal the enclosure 101. In some examples, the fill port 142 is welded using a laser beam. This weld can generate some metallic projections. Containment of such metallic projections and the laser beam is important in order to minimize, if not avoid, damage to the device electronics (such as, for instance, one or more of the internal components 150A, 150B, 150C, 150D) within the enclosure 101 during welding.

In some examples, the weld protection feature 140 includes a wall 144 machined within the enclosure 101 and positioned proximate the fill port 142 of the enclosure 101. The wall 144 is positioned with respect to the fill port 142, in some examples, to inhibit weld debris from damaging an electronic component (such as, for instance, one or more of the internal components 150A, 150B, 150C, 150D) of the implantable medical device 100 within the enclosure 101 during welding of the fill port 142. That is, in some examples, the wall 144 is positioned to block weld debris from reaching the electronic components (such as, for instance, one or more of the internal components 150A, 150B, 150C, 150D) within the enclosure 101. In some examples, the wall 144 is spaced from the fill port 142 to form a passageway 146 in between the wall 144 and the outside wall of the enclosure 101 to allow for fluid coupling of the fill port 142 and the interior of the enclosure 101. In this way, in some examples, any weld debris generated during the welding process can enter the passageway 146 but is stopped by the wall 144, thereby reducing the likelihood that any of the weld debris comes into contact with one or more of the internal components 150A, 150B, 150C, 150D within the enclosure 101.

For welding protection, typically, a titanium strip is used to protect the inner electrical components from any metallic ejections that may occur during the welding process. This strip is often welded to the enclosure or the lid of the device or secured to the assembly by a plastic nest. In some examples, by integrally incorporating the weld protection feature 140 within the enclosure 101 (for instance, by machining the weld protection feature 140 within the enclosure 101 itself), the need for any such separate strip to be attached to the enclosure at a later stage is eliminated. In this way, the steps needed to assemble the implantable medical device 100 are reduced, which allows for a more repeatable process by which to provide protection of one or more of the internal components 150A, 150B, 150C, 150D within the enclosure 101 during welding procedures.

Although the examples of FIGS. 1-5C show all of the internal integral features 110, 120, 130, 140 incorporated within the enclosure 101, it is important to note that this is not intended to be limiting. That is, the enclosure 101, in various examples, can include only one of the internal integral features 110, 120, 130, 140; can include a combination of two or more of the internal integral features 110, 120, 130, 140, or can include all of the internal integral features 110, 120, 130, 140. In further examples, the enclosure 101 can include two or more of any one of the internal integral features 110, 120, 130, 140.

Figure 6:
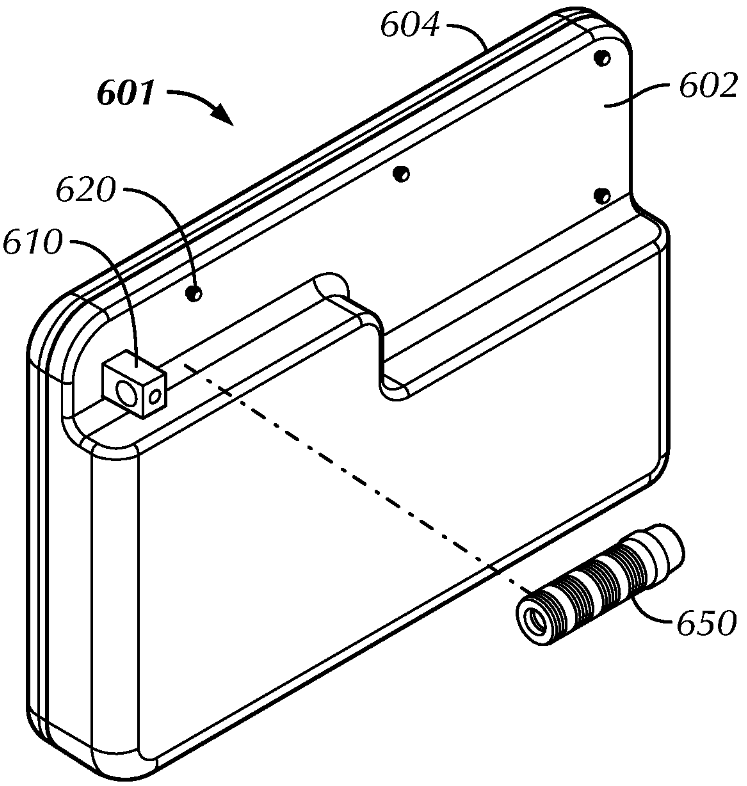
FIG. 6 is a perspective view of an enclosure for an implantable medical device, the enclosure being in accordance with at least one example of the invention.

Referring now to FIG. 6, in some examples, an enclosure 601 for an implantable medical device includes a first enclosure portion 602 and a second enclosure portion 604. In some examples, at least the first enclosure portion 602 and the second enclosure portion 604 are joined together to form the enclosure 601. In some examples, the enclosure 601 can be similar and/or include similar features to those described above with respect to the enclosure 101.

In some examples, the enclosure 601 includes at least one feature 610 configured for attachment of at least one component 650 of the implantable medical device to the enclosure 601. In some examples, the at least one feature 610 is integrally formed with the enclosure 610. In further examples, the enclosure 601 is machined to integrally form the at least one feature 610 with the enclosure 601. In other examples, the enclosure 601 can be formed in other ways, including, but not limited to, three-dimensional printing, metal injection molding, or the like, either instead of or in addition to machining.

In some examples, the integral feature 610 of the enclosure 601 includes an external integral feature 610 (that is, external to the enclosure 601). In some examples, the at least one feature 610 includes at least one external attachment member 610 formed on an exterior of at least one of the first enclosure portion 602 and the second enclosure portion 604. In further examples, the at least one external attachment member 610 is configured to attach the at least one component 650 to an exterior of the enclosure 601.

In some examples, the at least one external attachment member 610 includes at least one lead stack assembly attachment member 610 machined within the exterior of at least one of the first enclosure portion 602 and the second enclosure portion 604. In some examples, the at least one lead stack assembly attachment member 610 is configured to attach the component 650 to the enclosure 601 of the implantable medical device, the component 650 including a lead stack assembly 650. In some examples, the lead stack assembly 650 can be coupled to the lead stack assembly attachment member 610, which is integrally formed with the enclosure 601, and then a material, such as, but not limited to, epoxy, can be formed around the lead stack assembly 650 and the lead stack assembly attachment member 610 (and any other components, such as, but not limited to, an antenna) to form a header of the implantable medical device (for instance, similar to the header 106 of the implantable medical device 100 described herein).

For the fixation of a lead of a typical implantable medical device, usually a mechanical fixation connector (which has a female screw) is added to a lead cavity assembly to fixate the lead in place by means of a screw when inserted in the device. This stack is manufactured as a subassembly and then is placed in the header during the epoxy casting process. The lead stack assembly attachment member 610 being integrally formed with the enclosure 601, in some examples, eliminates this need for a separate mechanical fixation connector in typical implantable medical devices. By integrally including the lead stack assembly attachment member 610 as part of the enclosure 601, it eliminates the need for a mechanical fixation connector as a separate part and therefore simplifies the assembly process of the implantable medical device and reduces the cost of the parts. Also, integrally including the lead stack assembly attachment member 610 as part of the enclosure 601 allows for a more controlled and repeatable assembly of the header of the implantable medical device and reduces the risk of components exposure.

In some examples, the enclosure 601 includes at least one feature 620 configured for attachment of a header (for instance, similar to the header 106 of the implantable medical device 100 of FIG. 1) to the enclosure 601. In some examples, the at least one feature 620 is integrally formed with the enclosure 610. In further examples, the enclosure 601 is machined to integrally form the at least one feature 620 with the enclosure 601. In other examples, the enclosure 601 can be formed in other ways, including, but not limited to, three-dimensional printing, metal injection molding, or the like, either instead of or in addition to machining.

In some examples, the integral feature 620 of the enclosure 601 includes an external integral feature 620 (that is, external to the enclosure 601). In some examples, the at least one feature 620 includes at least one external attachment member 620 formed on an exterior of at least one of the first enclosure portion 602 and the second enclosure portion 604. In further examples, the at least one external attachment member 620 is configured to attach the at least one component, such as, but not limited to, a header, to an exterior of the enclosure 601.

In some examples, the at least one external attachment member 620 includes at least one header attachment member 620 machined within the exterior of at least one of the first enclosure portion 602 and the second enclosure portion 604. In some examples, the at least one header attachment member 620 is configured to at least partially attach the header to the enclosure 601 of the implantable medical device. In some examples, the at least one header attachment member 620 includes one or more pins, brackets, or the like extending from an exterior of the enclosure 601 configured to promote adhesion of the header to the enclosure 601 with overmolding or other forming of the header onto the enclosure 601. In some examples, the at least one header attachment member 620 includes an undercut feature to allow the header to form within the undercut feature to enhance adhesion of the header to the at least one header attachment member 620 and, in turn, the enclosure 601. In the example shown in FIG. 6, the enclosure 601 includes four header attachment members 620 disposed on an exterior of the first enclosure portion 602 for attachment of the header to the first enclosure portion 602. In other examples, the enclosure 601 can include more or less than four header attachment members 620, depending on at least the size and/or configuration of the header and/or the amount of adhesion needed to maintain attachment of the header to the enclosure 601. In still other examples, the one or more header attachment members 620 can be disposed on an exterior of the second enclosure portion 604 instead of or in addition to the first enclosure portion 602 depending upon the size and/or configuration of the header. In some examples, the one or more header attachment members 620 are integrally formed with the enclosure 601 and then a material, such as, but not limited to, epoxy, can be formed around the one or more header attachment members 620 to form the header of the implantable medical device (for instance, similar to the header 106 of the implantable medical device 100 described herein).

Figure 7:
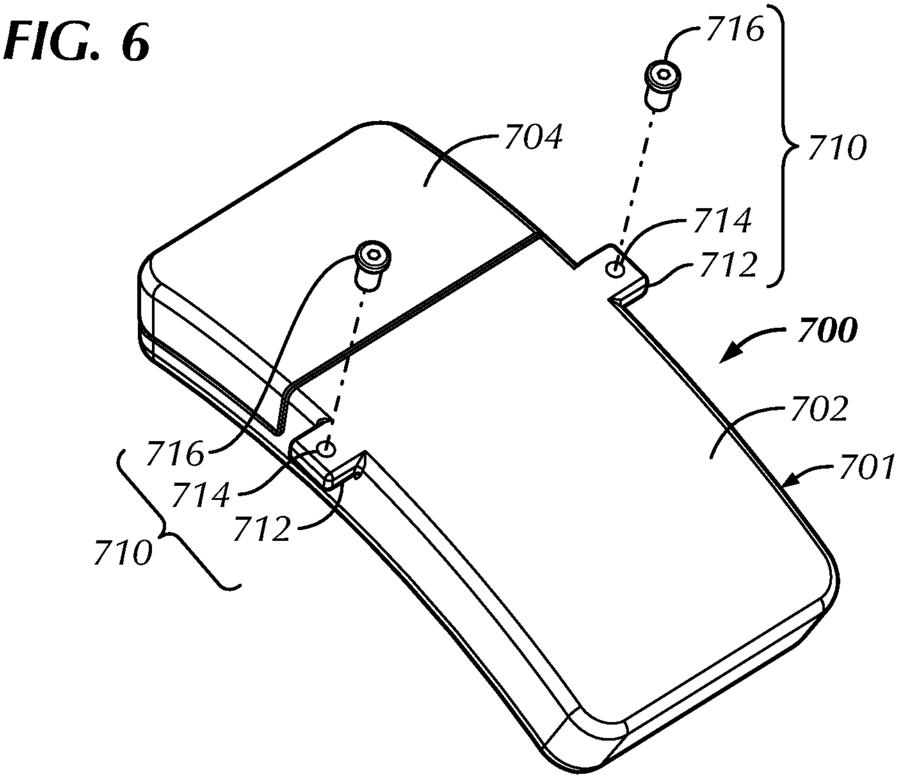
FIG. 7 is a perspective view of an enclosure for an implantable medical device, the enclosure being in accordance with at least one example of the invention.

Referring now to FIG. 7, in some examples, an enclosure 701 for an implantable medical device 700 includes a first enclosure portion 702 and a second enclosure portion 704. In some examples, at least the first enclosure portion 702 and the second enclosure portion 704 are joined together to form the enclosure 701.

In some examples, the enclosure 701 includes at least one feature 710 configured for attachment of the implantable medical device 700 to a patient. In some examples, the at least one feature 710 is integrally formed with the enclosure 710. In further examples, the enclosure 701 is machined to integrally form the at least one feature 710 with the enclosure 701. In other examples, the enclosure 701 can be formed in other ways, including, but not limited to, three-dimensional printing, metal injection molding, or the like, either instead of or in addition to machining.

In some examples, the integral feature 710 of the enclosure 601 includes an external integral feature 710. In some examples, the at least one feature 710 includes at least one external attachment member 710 integrally formed on an exterior of at least one of the first enclosure portion 702 and the second enclosure portion 704.

In some examples, the at least one external attachment member 710 includes at least one attachment tab 712 machined within at least one of the first enclosure portion 702 and the second enclosure portion 704. In some examples, the at least one attachment tab 712 is configured to attach the implantable medical device 700 to a patient. In some examples, the enclosure 701 includes two attachment tabs 712. In other examples, the enclosure 701 can include more than two attachment tabs 712. The one or more attachment tabs 712, in some examples, are configured to allow for attachment of the implantable medical device 700 to the patient. In further examples, the one or more attachment tabs 712 allow for attachment of the implantable medical device 700 to a bone of the patient. In still further examples, the one or more attachment tabs 712 allow for attachment of the implantable medical device 700 to a skull of the patient.

In some examples, the one or more attachment tabs 712 each includes a hole 714 through the tab 712 to allow for a fastener 716 to pass through the hole 714 and allow fastening of the fastener 716 within a portion of the patient (such as, but not limited to, a bone of the patient). The fastener 716, in some examples, can include, but is not limited to, a screw. In this way, in some examples, the implantable medical device 700 can be attached to the patient using the one or more fasteners 716 through the one or more attachment tabs 712 integrally formed with the enclosure 701 of the implantable medical device 700 and into a portion (such as a bone, for instance) of the patient.

For fixation of a typical implantable medical device, a separate tab must be added to the implantable medical device to be able to fasten it directly to a bone of the patient. This tab can typically be either part of a separate holder or cradle that engages with and retains the implantable medical device or welded directly to the enclosure of the implantable medical device. By integrally forming the one or more attachment tabs 712 to the enclosure 701 itself, it removes the need for a separate holder or the welding or otherwise attaching of a separate tab as a separate process. Such an attachment member 710 integrally formed with the enclosure 701 can, in some examples, simplify a device assembly process, as well as also simplifying an implant procedure.

The present inventors have recognized various advantages of the subject matter described herein. The present inventors have recognized, among other things, that the present subject matter can be used to provide an enclosure for a medical device including integral features of the enclosure configured to fix, maintain, and/or self-center inner components of the medical device and remove the need for (or at least to reduce the size or importance of) a plastic nest within the enclosure. In various examples, such integral features can reduce assembly processes and therefore improve yield with respect to the enclosure. In some examples, the present subject matter is advantageous in that it provides for the addition of inner features to metallic enclosures by manufacturing them through machining, in some examples, in order to reduce, if not eliminate, the need for one or more inner components of the medical device. In some examples, the present invention facilitates reduction of overall volume of the medical device, reduction of the number of assembly stages for the medical device, and/or mitigation of assembly risks that can compromise quality of the medical device. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A device enclosure for an Implantable medical device, the implantable medical device including at least one component, the device enclosure comprising:

a) first enclosure portion having a first outer surface spaced from a first inner surface;

b) a second enclosure portion having a second outer surface spaced from a second inner surface, wherein at least the first enclosure portion and the second enclosure portion are joined together to form the device enclosure;

c) a fill port extending through one of the first and second enclosure portions, wherein the fill port is aligned along an imaginary axis;

d) a wall extending from one of the first and second inner surfaces of the respective first and second enclosure portion having the fill port;

e) a passageway residing between the fill port at the one of the first and second inner surfaces of the respective first and second enclosure portion and the wall, wherein the imaginary axis aligned with the fill port extends across the passageway to intersect the wall; and f) a weld at the fill port to seal the enclosure.

2. The enclosure of claim 1, wherein the one of the first and second enclosure portions having the fill port is characterized as having been machined to form the wall as an integral wall extending from the one of the first and second inner surface of the respective first and second enclosure portion having the fill port.

3. The enclosure of claim 1, wherein the at least one component includes an internal component of the implantable medical device.

4. An implantable medical device comprising:

a) a device enclosure including:

i) first enclosure portion having a first outer surface spaced from a first inner surface; and ii) a second enclosure portion having a second outer surface spaced from a second inner surface, wherein at least the first enclosure portion and the second enclosure portion are joined together to form the device enclosure;

b) at least one component housed inside the device enclosure;

a fill port extending through one of the first and second enclosure portions, wherein the fill port is aligned along an imaginary axis;

d) a wall extending from one of the first and second inner surface of the respective first and second enclosure portion having the fill port; and e) a passageway residing between the fill port at the one of the first and second inner surface of the respective first and second enclosure portion and the wall, wherein the imaginary axis aligned with the fill port extends across the passageway to intersect the wall.

5. The implantable medical device of claim 4, wherein the enclosure is machined to form the wall as an integral wall extending from the one of the first and second inner surface of the respective first and second enclosure portion having the fill port.

6. An implantable medical device comprising:

a machined enclosure including:

i) a first enclosure portion; and ii) a second enclosure portion, wherein at least the first enclosure portion and the second enclosure portion are joined together to form the enclosure;

b) at least one electronic component housed inside the device enclosure;

c) a fill port extending through one of the first and second enclosure portions, wherein the fill port is aligned along an imaginary axis;

d) an integral wall extending from one of the first and second inner surface of the respective first and second enclosure portion having the fill port; and e) a passageway residing between the fill port at the one of the first and second inner surface of the respective first and second enclosure portion and the integral wall, wherein the imaginary axis aligned with the fill port extends across the passageway to intersect the integral wall.

7. The implantable medical device of claim 6, wherein the weld integral wall is configured to inhibit weld debris from damaging the electronic component housed inside the device enclosure during welding of the fill port.

* * * * *